United States Patent [19]
Paradis

[11] Patent Number: 5,509,433
[45] Date of Patent: Apr. 23, 1996

[54] CONTROL OF FLUID FLOW

[76] Inventor: Joseph R. Paradis, 17 Hickory Forest Dr., Hilton Head Island, S.C. 29926

[21] Appl. No.: 135,673

[22] Filed: Oct. 13, 1993

[51] Int. Cl.⁶ .................................................. A61M 39/00
[52] U.S. Cl. .......................... 137/1; 251/149.1; 604/249
[58] Field of Search ........................... 251/149.8, 149.1, 251/149.6; 137/540, 843, 1; 222/544, 563, 559, 518; 604/249, 905, 247

[56] References Cited

U.S. PATENT DOCUMENTS

| | | | |
|---|---|---|---|
| 3,503,418 | 3/1970 | Petrucci et al. | 137/540 X |
| 3,976,278 | 8/1976 | Dye et al. | 251/149.6 |
| 4,445,539 | 5/1984 | Credle | 251/149.6 X |
| 4,681,132 | 7/1987 | Lardner | 137/843 X |
| 4,710,168 | 12/1987 | Schwab et al. | 251/149.1 X |
| 4,908,018 | 3/1990 | Thomsen | 604/247 X |
| 4,948,014 | 8/1990 | Rutter et al. | 251/149.6 X |
| 5,046,645 | 9/1991 | Hagan et al. | 251/149.6 X |
| 5,163,922 | 11/1992 | McElveen, Jr. et al. | 251/149.1 X |
| 5,215,538 | 6/1993 | Larkin | 251/149.1 X |
| 5,255,713 | 10/1993 | Scholle et al. | 251/149.6 X |

*Primary Examiner*—John Rivell
*Assistant Examiner*—Kevin L. Lee
*Attorney, Agent, or Firm*—George E. Kersey

[57] ABSTRACT

A flow control device with an inlet for the flow of fluid and a movable member sealing the inlet and having a flexible body for controlling flow by the extent to which the flexible body of the movable member is buckled. The movable member extends between the inlet and an outlet and is expandable laterally with respect to the axis of a channel for the outlet in order to control flow. A member external to the flow control device can activate the moveable member which can take the form of a plug seated in the inlet by depressing the plug from its seat. The movable member also can be bell-shaped with its upper portion sealing the inlet and slotted walls straddling the outlet.

18 Claims, 12 Drawing Sheets

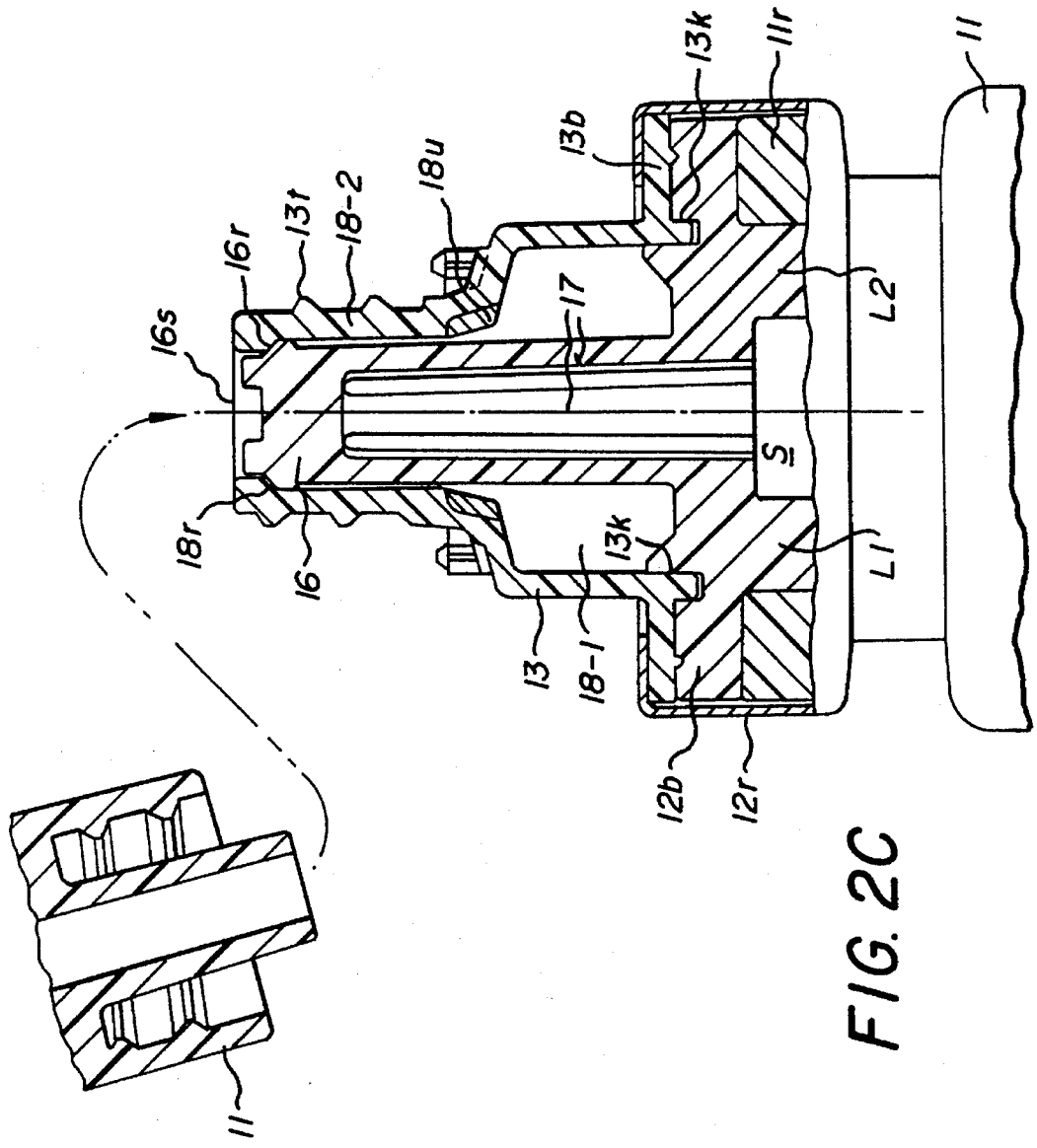

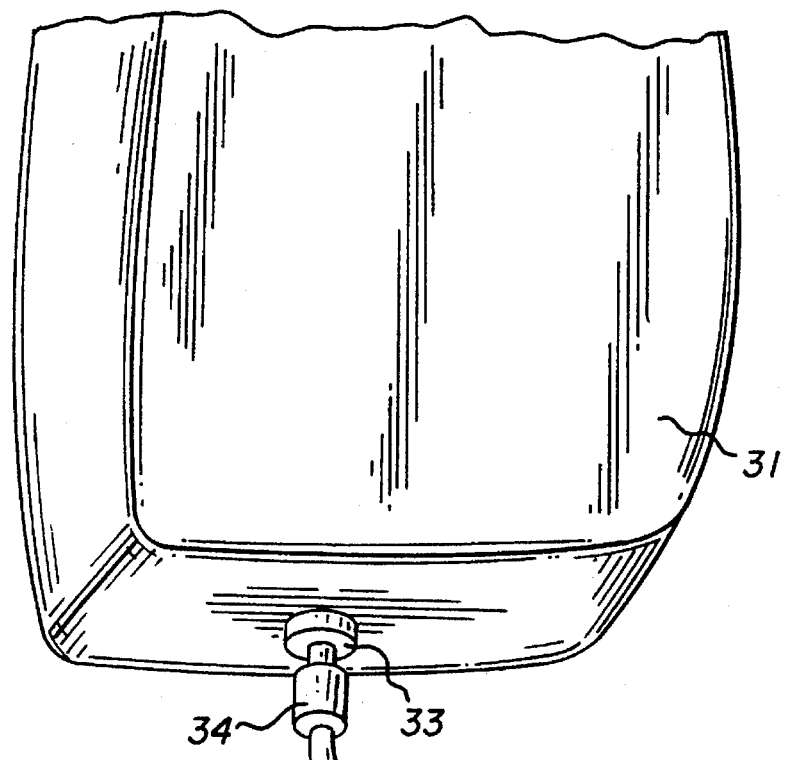
FIG. 3
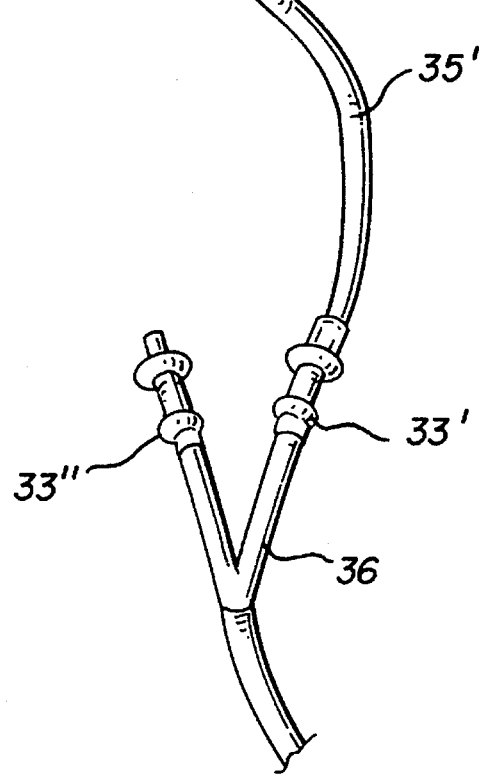

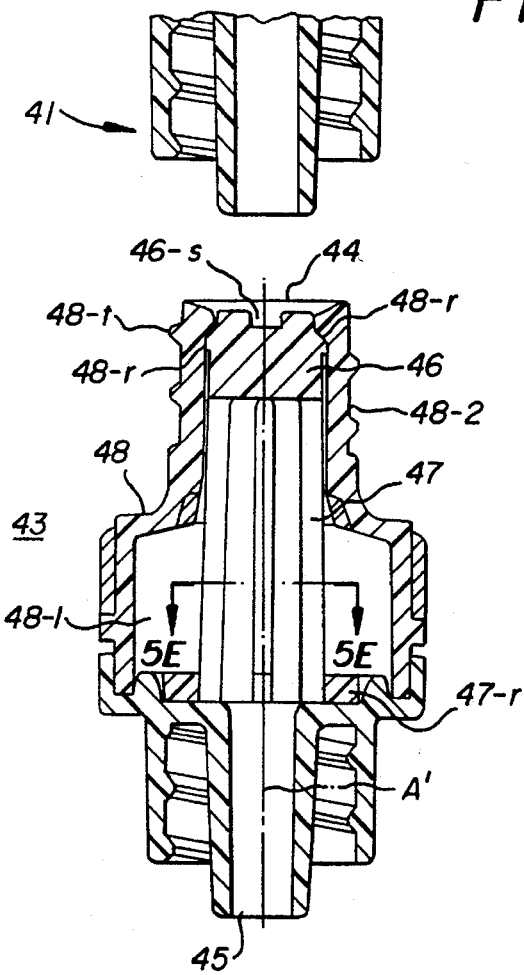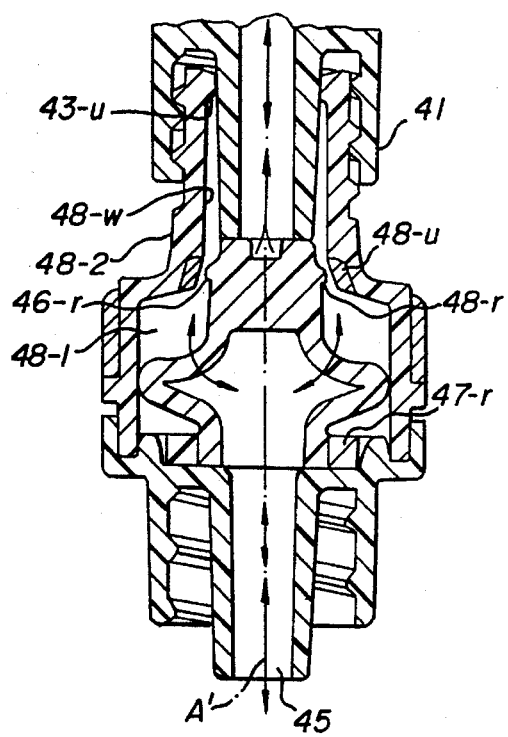
FIG. 4B
FIG. 4A
FIG. 4C

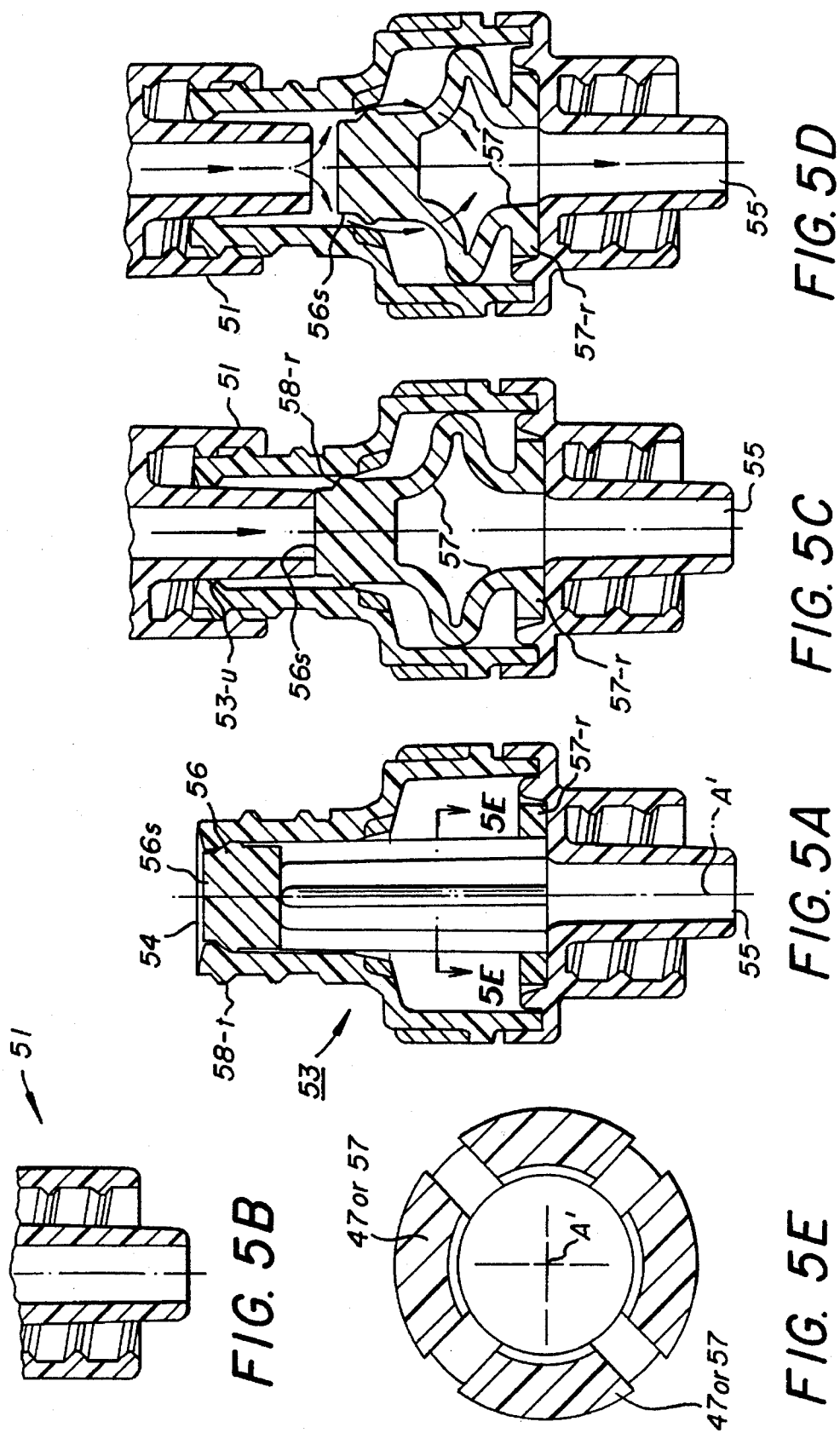

CONTROL OF FLUID FLOW

BACKGROUND OF THE INVENTION

This invention relates to flow control and more particularly, to the control of fluid flow from containers of medical solutions, and with respect to the infusion and aspiration of fluids in venous and arterial systems.

A common container for medical fluids is a plastic pouch which contains saline, i.e. a salt solution used in investigation of biological and physiological processes. Such a container is "spiked", i.e. pierced by a projection, in order to access its contents which are carried by a conduit, typically plastic tubing, through a "check" valve that is used to prevent backflow to the spiked container. In addition, other check valves can be used with the conduit to provide for the infusion and/or aspiration of other substances, such as medicaments, body fluids, and anesthetics. Infusion is commonly used to introduce saline or other medical fluids into veins, while aspiration is commonly used to draw fluids from body cavities.

The ordinary check valve used with conduits from medicinal containers functions by the deflection of an elastomeric element towards and away from a valve seat. The deflection is towards the valve seat in order to prevent flow, and away from the seat to permit flow.

Because the conventional saline bag is spiked, removal of the spiking connector is accomplished with difficulty. Unless the bag is inverted, there will be leakage when the spike is withdrawn.

In some cases the control of fluid flow is with respect to a multiplicity of channels that have varying degrees of convergence with one another. A typical multichannel arrangement makes use of connectors which permit the intercoupling of flow channels. For example, when two channels are to be joined to permit a common output, the connector can take the form of a fitting that resembles a "Y". When one of the channels terminates in an infusion site, the prior practice has been to access the site by needles, which are undesirable.

Because of the desirability of achieving needless injection and infusion of fluids, one effort has resulted in Rogers et al. U.S. Pat. No. 5,006,114 of Apr. 9, 1991 in which a valve assembly has a Luer lock on an inlet, and movable piston seals the inlet.

When a syringe is attached to the Rogers inlet the piston is displaced to unseal a fluid channel which connects the end of the syringe to an outlet, and then to a device connected to a patient. When the syringe is removed from the inlet the piston is moved to its original closed position by an internal spring of the valve. This device suffers from the disadvantage that the requirement of a spring for acting against the piston results in a force against the inserted Luer tip that increases as the piston is displaced.

In addition, the Rogers medical valve assembly provides an outlet channel that is displaced at an angle in relation to the inlet. As a consequence of this angular displacement, it is difficult to manufacture the device since there is a tendency for flash to accumulate at the entrance of the outlet channel in the vicinity of the piston. In addition, the angular configuration of the Rogers valve does not lend itself to manifold application.

Moreover, the Rogers design is intended for a Luer fitting which does not have a taper so that when the conventional tapered Luer fitting is employed, it can become jammed in the straight line walls of the inlet.

An attempt to overcome the disadvantages of Rogers is disclosed in Raines, U.S. Pat. No. 5,147,333, which issued Sep. 15, 1992. In the Raines patent there is accommodation for a tapered Luer fitting, but there is the continued disadvantage of the necessity for using a spring to urge a piston or spool forwardly during closure of the valve and rearwardly when the valve is being opened.

As a result, the disadvantageous increase in spring force with displacement continues to be present. Furthermore, the Raines "backcheck" valve requires a pair of vertically offset ports that extend laterally from a tubular body and the spool or piston is disposed between the ports. In addition, like the predecessor Rogers valve the piston or spool in Raines requires at least one projection from the end of the piston contacted by a Luer tip in order to permit the flow of fluid from the Luer tip through the valve.

Furthermore, like the Rogers predecessor, the Raines valve is subject to difficulties in manufacture because of flash since the various outlet ports are angularly, i.e., perpendicularly, oriented in relation to their inlets.

Accordingly, it is an object of the invention to achieve needless injection, infusion and aspiration without the need for spring-loaded members, such as pistons or spools where the counterforce exerted by the spring increases as the piston is displaced. A related object of the invention is to overcome the disadvantages characterizing the needless injection valves of Rogers, U.S. Pat. No. 5,006,114 and Raines, U.S. Pat. No. 5,147,333.

A further object of the invention is to overcome the need for angular orientation of an outlet in relation to an inlet in order to avoid manufacturing difficulties such as the creation of flash which can clog or reduce the volume of fluid flow from an inlet to an outlet.

Yet another object of the invention is permit the non-use of projections on a closure for an inlet, whereby a Luer fitting can open an inlet channel without the need for engaging one or more projections on a closure.

Other arrangements are disclosed in Newgard, U.S. Pat. No. 5,064,416; Sivert, U.S. Pat. No. 4,915,687 and Jackson, U.S. Pat. No. 4,429,856. There arrangements are complex and difficult to manufacture with numerous disadvantages.

Another objection to existing arrangements is that their activators are not interchangeable. Thus injection sites that require needle injection cannot be used without needles; conversely injection sites that are externally actuated by inserting a member that opens a diaphragm cannot be used with needles. In addition, the non-needle injection sites present problems of sterility. In order to have external access to the control diaphragm, it is necessary to have an open channel that can become contaminated. Even when a temporary seal is provided for the open channel, removal of the seal prior to injection allows inadvertent contamination. This is by contrast with an injection site having a needle-puncturable surface. The latter can be wiped clean with a sterilizing agent before injection is to take place.

A further object of the invention to enhance the control that can be achieved over fluid flow. A related object is to enhance flow control where fluid infusion or combination is to take place.

An important object of the invention is to eliminate the need for needle usage at injection sites, while permitting needle usage if that is desired. A related object is to maintain sterility at injection sites that are operated without needles, while simultaneously permitting such sites to be used with needles if necessary.

An additional object of the invention is to improve the performance of valves for infusion, injection, aspiration and control of fluid flow.

A further object of the invention is to achieve temper evident arrangements for components used in the infusion and aspiration of medicinal fluids.

SUMMARY OF THE INVENTION

In accomplishing the foregoing and related objects the invention provides a flow control device with an inlet for the flow of fluid; an outlet connected to the inlet and disposed with respect thereto to serve as a conduit for flow into the inlet; and a movable member sealing the inlet and having a flexible body for controlling flow by the extent to which the flexible body of the movable member is buckled.

In accordance with one aspect of the invention, the movable member extends between the inlet and outlet and is expandable laterally with respect to the axis of the outlet in order to control flow.

A further member can be included for permitting the activation of the control member external to the flow control device, wherein the moveable member terminates in a plug seated at the mouth of the inlet and can be depressed from its seat.

The control member can be bell-shaped, with an upper portion sealing the inlet and walls straddling the outlet, while the extended control member can be bowed under pressure in the axial direction of said outlet channel.

The bell-shaped control member can have slotted walls which are bucked under pressure. The slotted walls can extend from a head sealing an inlet to a base encircling an outlet channel.

In accordance with a further aspect of the invention the head can have a level surface at the entrance to the inlet, or an interrupted surface at the entrance to the inlet.

In apparatus of the invention wherein a flow control device seals a container of medicinal fluid, access can be achieved by flexing a moveable sealing member to unseal the container, and removal of the flex can restore the seal of the container.

In a method of controlling fluid flow in accordance with the invention the steps can include (1) sealing an inlet channel by a flexible stopper; and (2) controllably flexing the stopper to permit the flow of fluid to an outlet.

The method can further include the step of flexing the stopper by applying fluid pressure thereto, or by applying mechanical pressure thereto. A further step can include positioning the stopper at the inlet of a container for medicinal fluid in order to permit access to the container by flexing the stopper, and resealing of the container by unflexing the stopper.

In the method the step of flexing the stopper can include the lateral expansion thereof with respect to axes of the inlet and outlet.

In a method of fabricating a flow control device, the steps can include (a) molding an inlet member having an axis of flow, a coaxial seat and an expansion chamber; (b) molding an outlet member having the axis of flow and a coaxial support; (c) inserting an expandable control member into the inlet member with respect to the seat; and (e) joining the outlet member to the inlet member, with the support for the expandable control member against the control member.

The method can further include the step of molding the control member of an elastomeric material, and the control member can extend longitudinally with the further step of longitudinally slotting the control member. The control member can have a circular body, with the slots uniformly spaced about the body.

DESCRIPTION OF THE DRAWINGS

First Embodiment

Second Embodiment

Figure 1A:
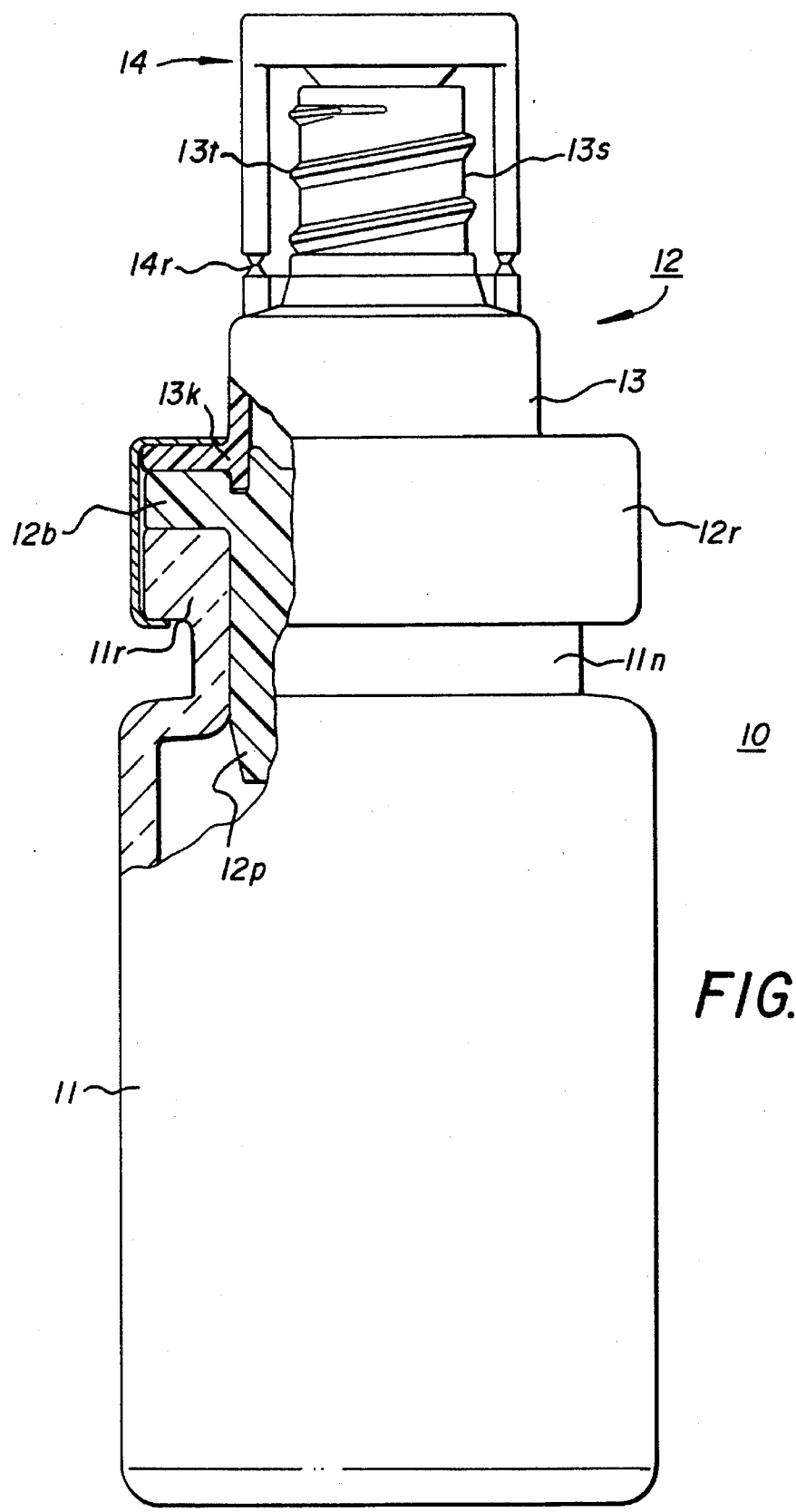
FIG. 1A is a plan view of a medicinal container with a stopper including a flow-control valve in accordance with the invention.
Figure 2A:
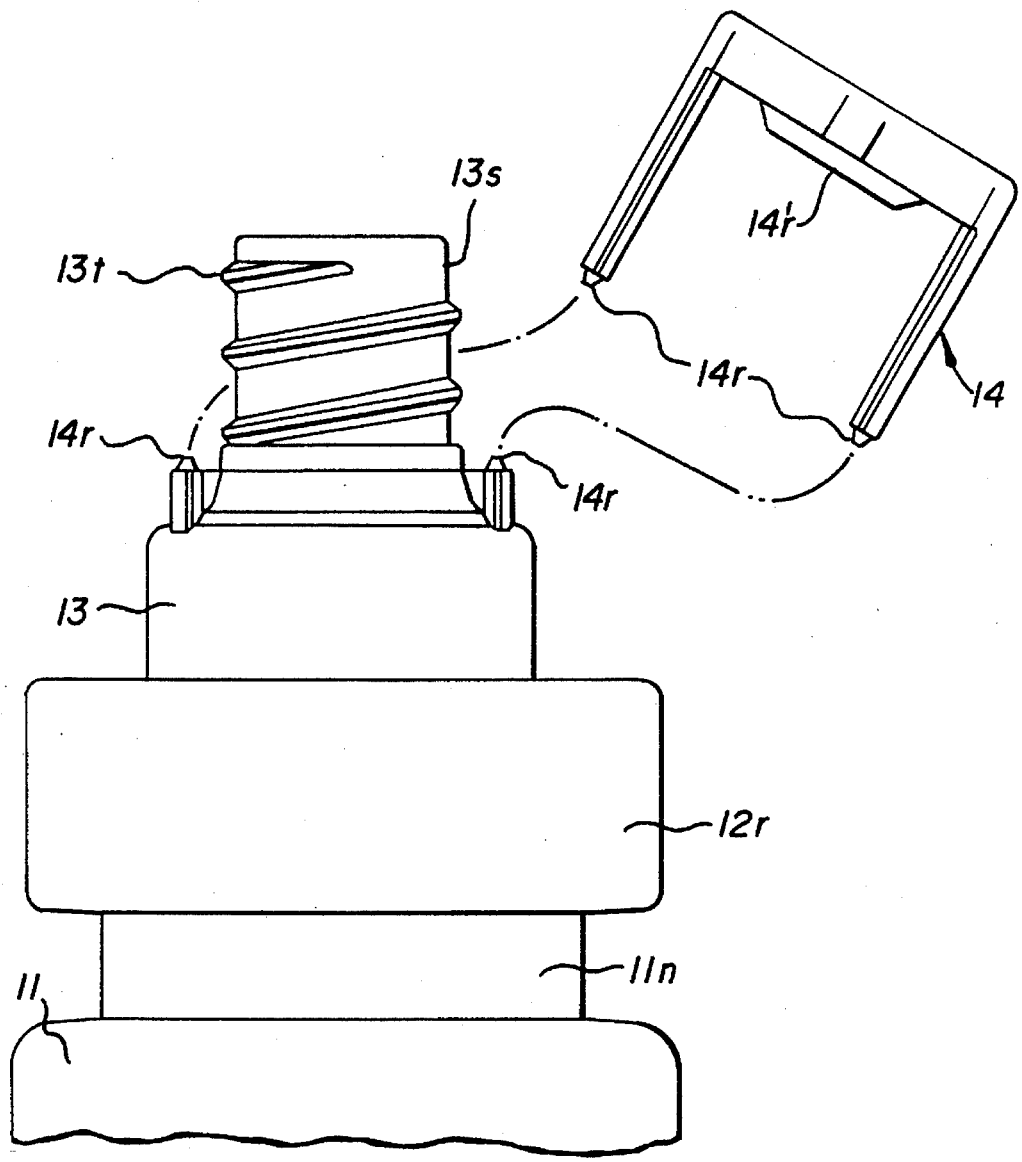
Figure 2D:
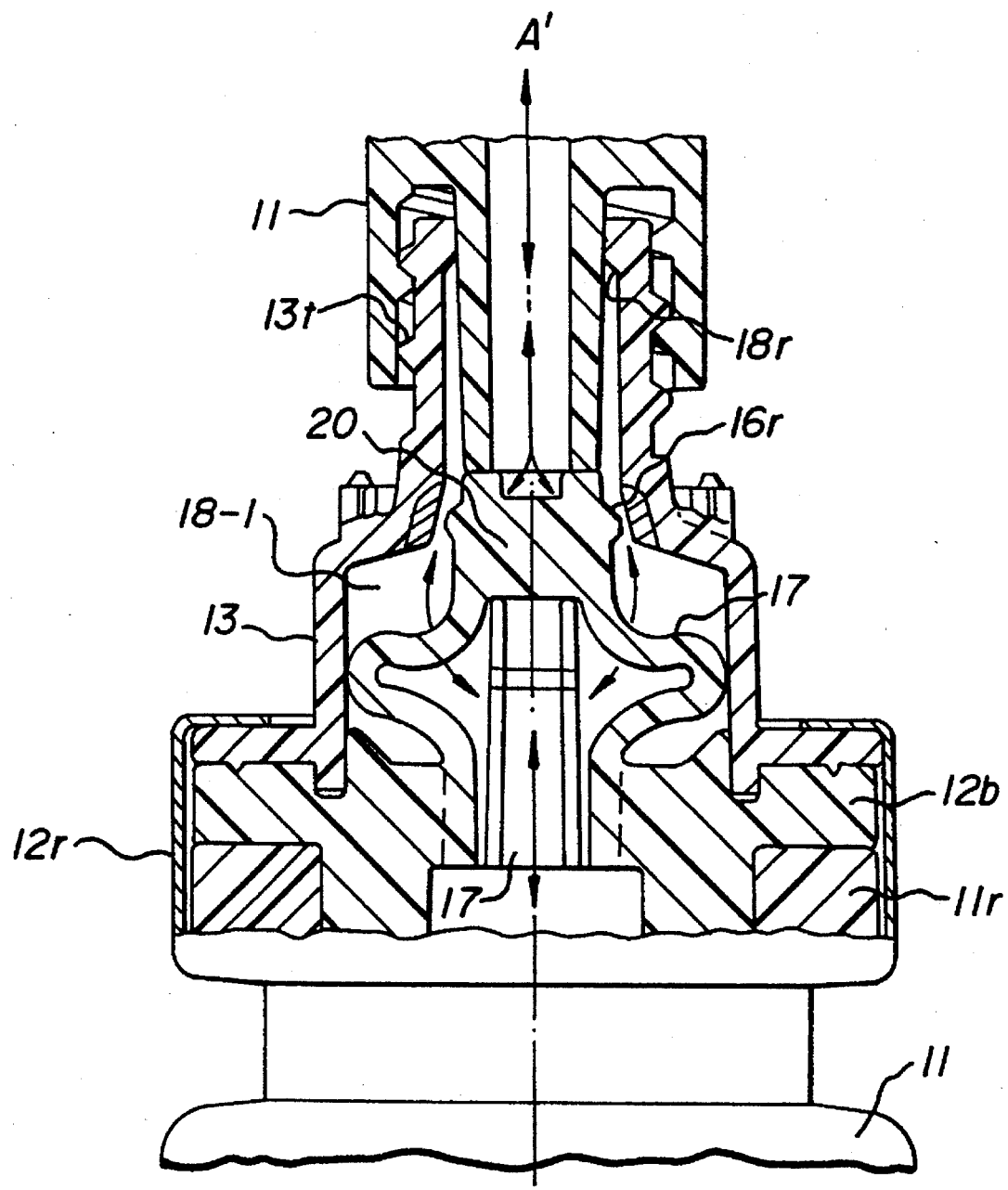

FIG. 2A is a partial view of the container of FIG. 1A illustrating the removal of a tamper evident sub-cap;

FIG. 2B is a sectional view of the engagement portion of a standard Luer lock fitting for use with the container of FIG. 2A;

FIG. 2C is a cross-sectional view of FIG. 2A illustrating a valve of the invention contained within the cap 12;

FIG. 2D is a cross-sectional view illustrating the operation of the valve contained within the cap of FIG. 2C by the Luer fitting of FIG. 2B.

Third Embodiment

FIG. 3 is a perspective view showing the invention being used with an infusion bag containing saline or other medicinal substance that is to be infused into a patient through a check valve of the invention accompanied by an auxiliary infusion valve of the invention.

Fourth Embodiment

FIG. 4A is a sectional view of a flow-control valve with an infusion site in accordance with the invention;

FIG. 4B is a partial view of a Luer activator for the flow control device of FIG. 4A;

FIG. 4C is a cross-sectional view of the infusion site device of FIG. 4A after being activated by the Luer activator of FIG. 4B.

Fifth Embodiment

FIG. 5A is a sectional view of an alternative flow-control valve with an infusion site in accordance with the invention;

FIG. 5B is a partial view of a Luer activator for the flow control device of FIG. 5A;

FIG. 5C is a cross-sectional view of the infusion site device of FIG. 5A during activation by the Luer activator of FIG. 5B;

FIG. 5D is a cross-sectional view of the infusion site device of FIG. 5A after activation by the Luer activator of FIG. 5B;

FIG. 5E is a cross-sectional view of an infusion site activator device in accordance with the invention taken along the lines A—A of FIG. 5A.

DETAILED DESCRIPTION

(A) FIRST EMBODIMENT OF THE INVENTION

Figure 1B:
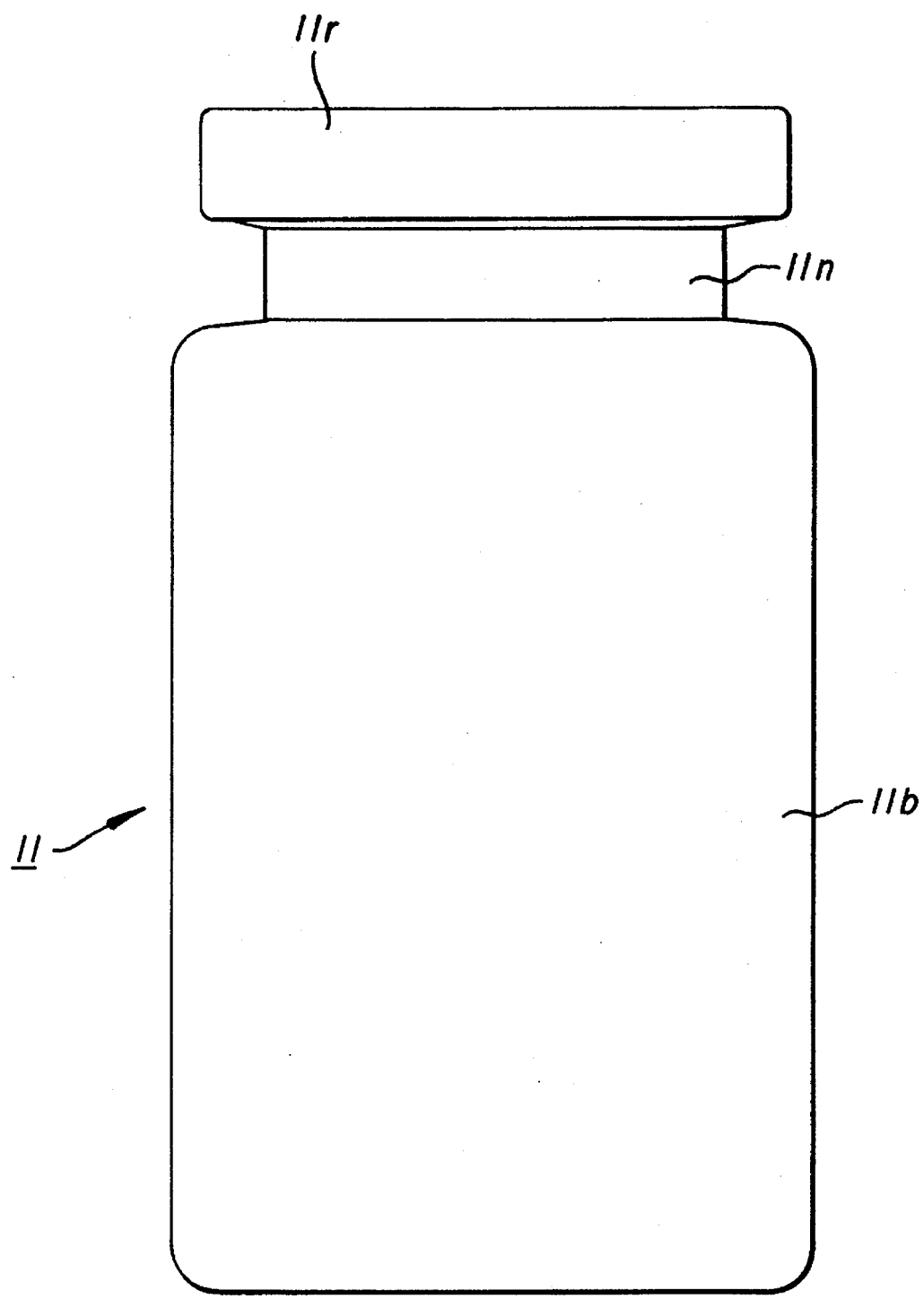
FIG. 1B is a is a plan view of the medicinal container of FIG. 1A before insertion of its stopper contained flow control device.

With reference to the drawings, a medicinal container 10 which is formed by a bottle 11 that is sealed to a cap 12, is shown in FIG. 1A. The region of the container 10 where the cap 12 is sealed to the bottle 11 is broken away to illustrate the mode of sealing. The bottle 11 is a standard container, as shown in FIG. 1B, with a body 11b extending to an inlet rim 11r by a neck 11n.

Figure 1C:
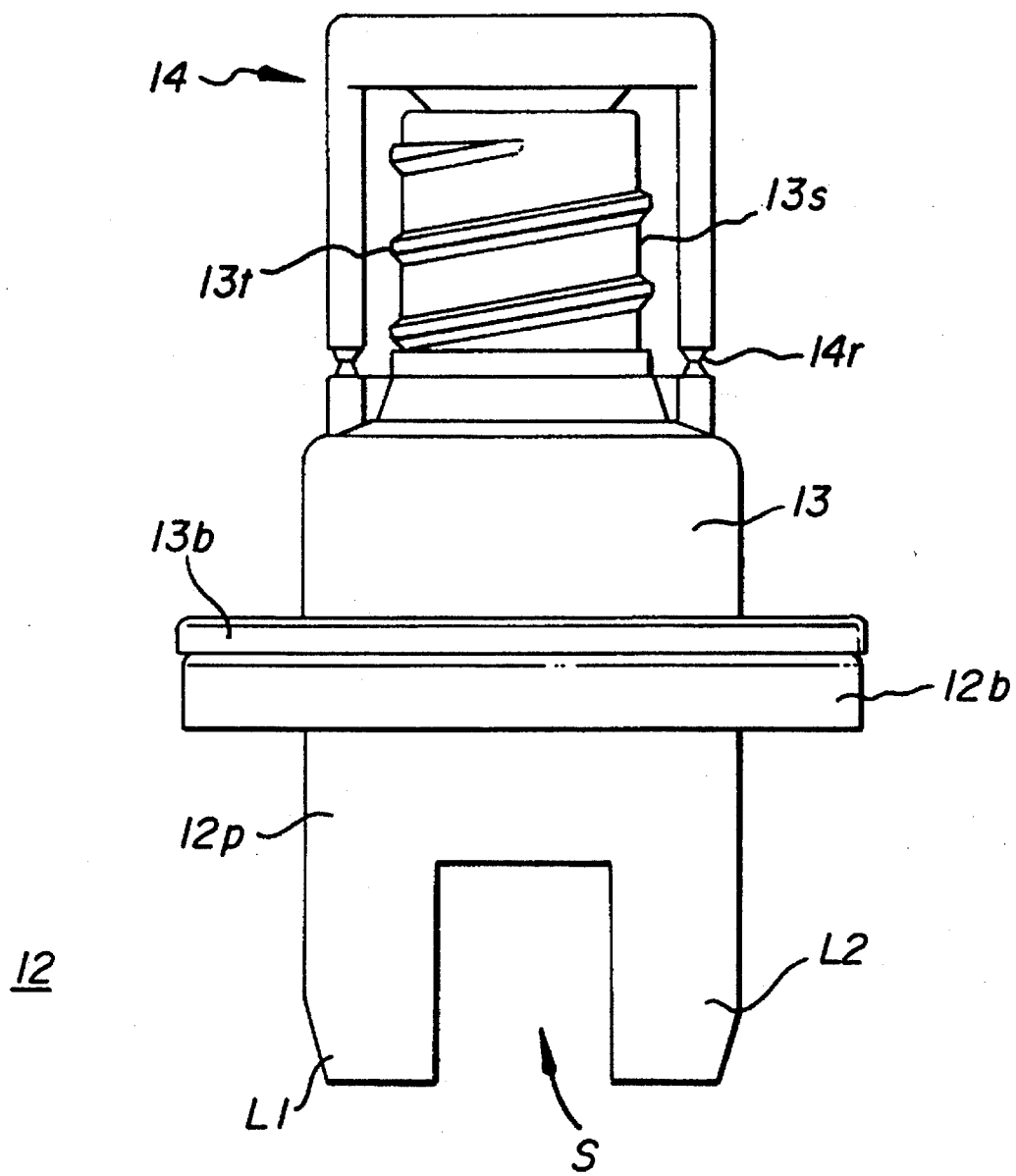
FIG. 1C is a plan view, before insertion into the container of FIG. 1B, of a stopper containing a flow control device of the invention.

The cap 12, as detailed in FIG. 1C, includes a stopper 12p that depends from a base 12b. The cap 12 includes an inlet housing 13 with a valve of the invention, as shown in the cross-sectional view of FIG. 1E.

The stopper 12p has opposed legs L1 and L2 straddling a spaced interval S. The housing 13 of the cap 12 has an inlet stem 13s which illustratively includes an exterior set of Luer threads 13t. The access opening of the inlet stem 13s is initially blocked by a tamper-evident seal 14. Details relating to the seal 14 are illustrated in FIGS. 1E and 1G, of which FIG. 1E is a sectional view of the top portion of the container of FIG. 1A, FIG. 1F is a top view of FIG. 1E before sectioning and FIG. 1G is a partial side view of FIG. 1F.

When access is desired to the interior of the cap 12 by way of the housing 13, the seal 14 is broken away at frangible regions 14r with the result that a Luer fitting can be threaded upon the inlet stem 13s in the fashion illustrated in FIGS. 2A through 2D.

Figure 1D:
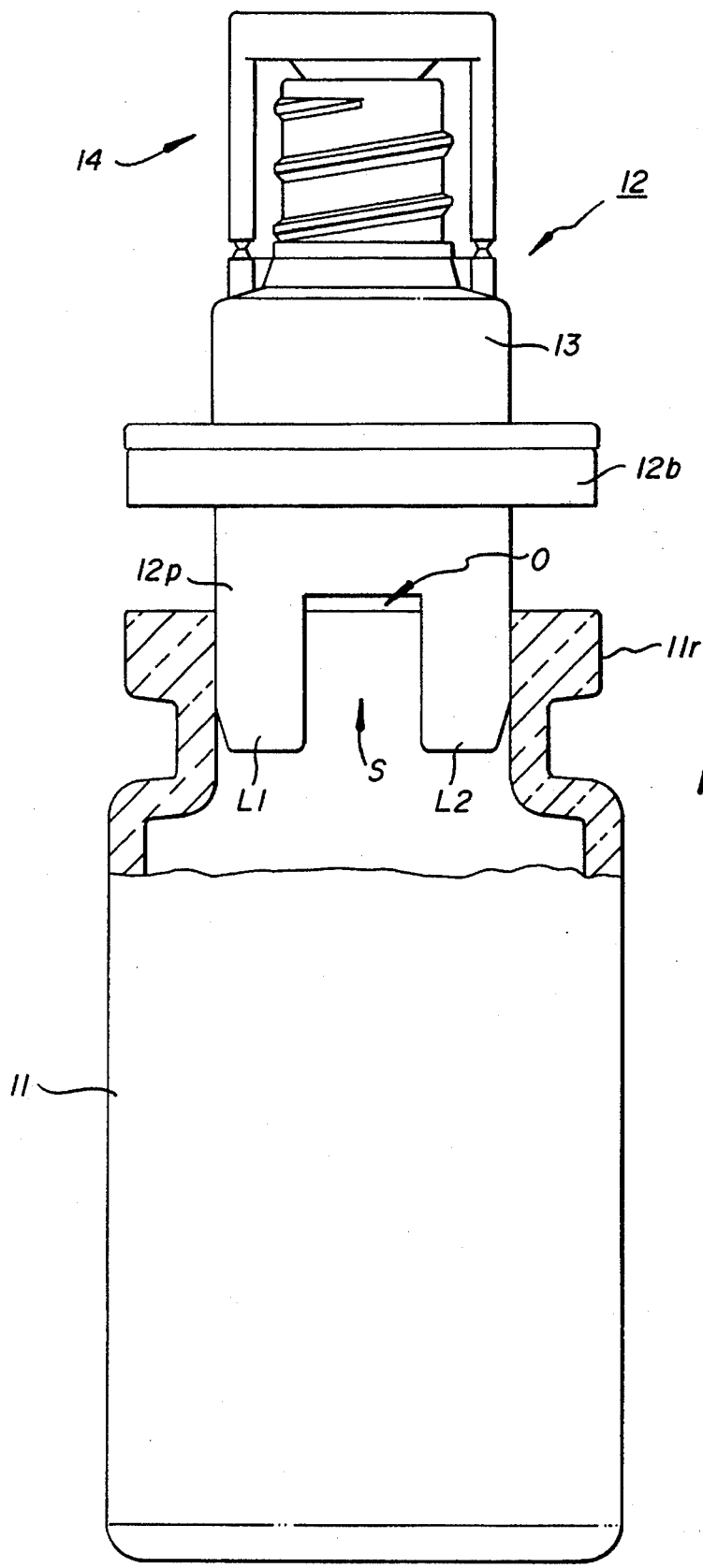
FIG. 1D is a plan view illustrating the partial insertion of the stopper of FIG. 1C, with its flow control device, into the container of FIG. 1B.
Figure 1E:
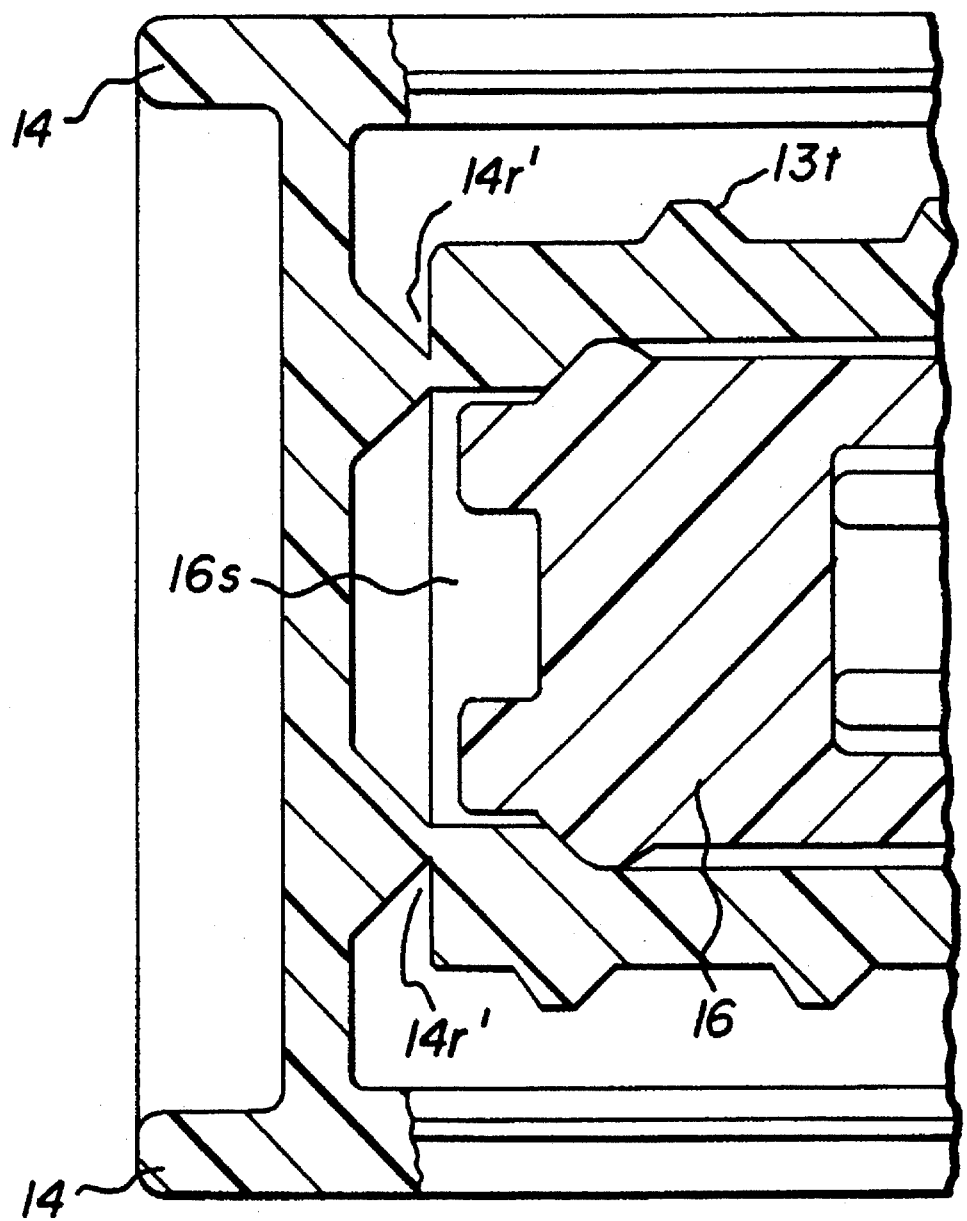
FIG. 1E is a sectional view of the top portion of the container of FIG. 1A.
Figure 1G:
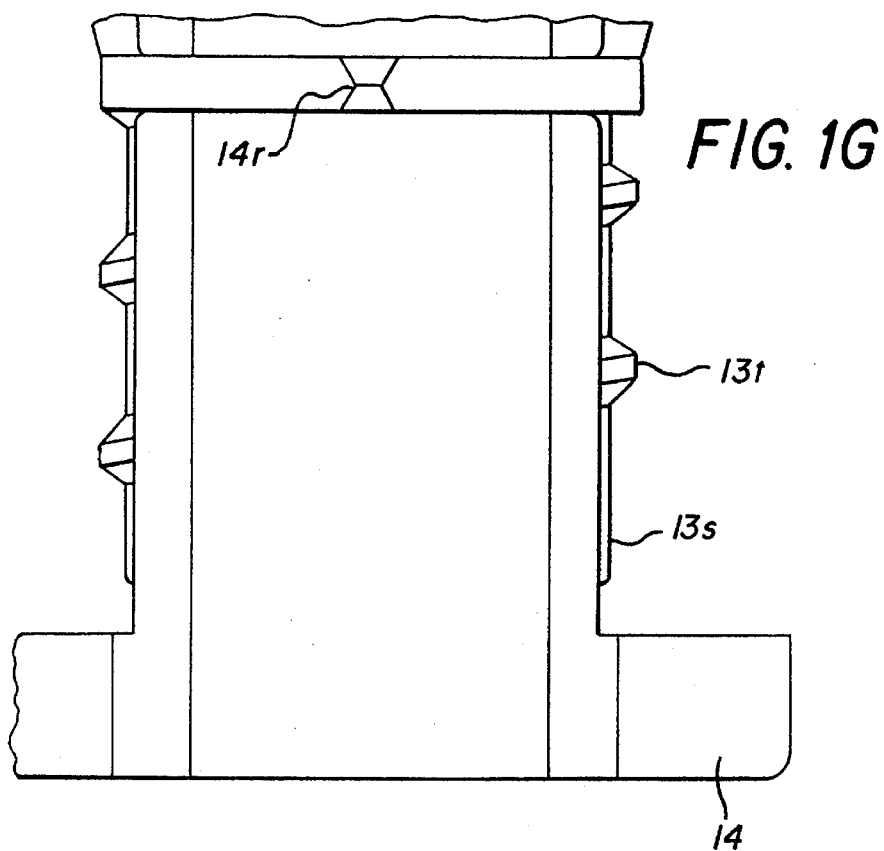
FIG. 1G is a partial side view of FIG. 1F.
Figure 1F:
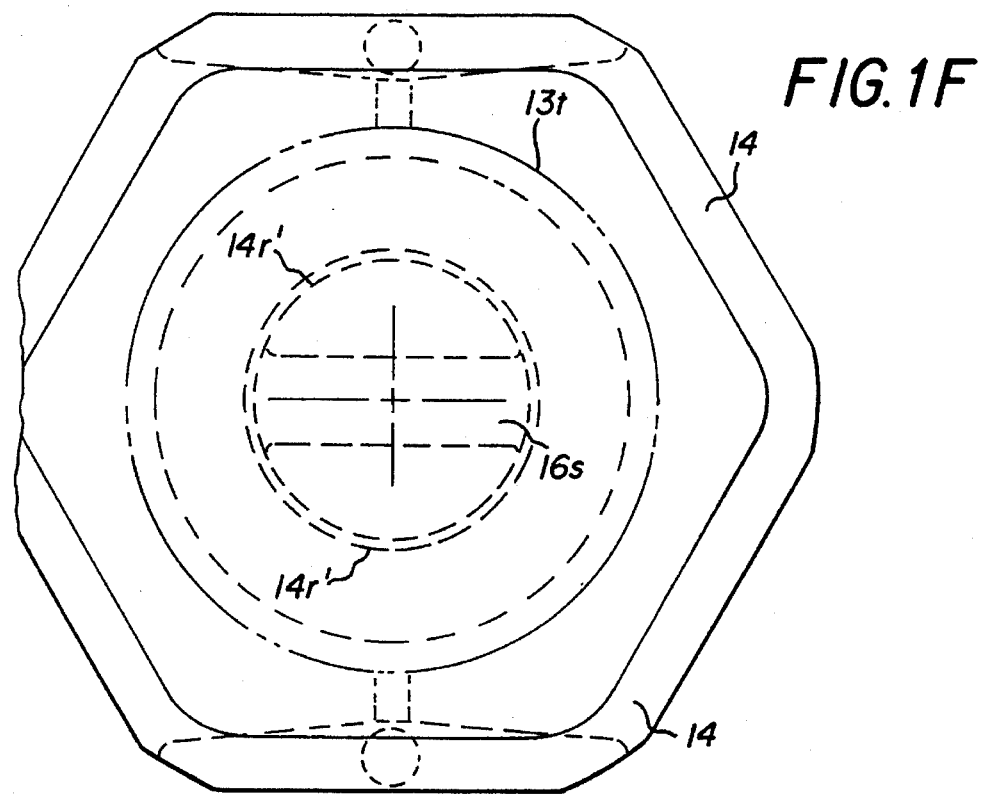
FIG. 1F is a top view of FIG. 1E before sectioning.

As shown in FIG. 1D, the cap 12, with the tamper-evident seal 14, is inserted into the container 11 at the rim 11r. It is to be noted in FIG. 1D that the stopper portion 12p is initially only partially inserted into the container 11, so that the slot S between the legs L1 and L2 of the stopper 12p allows access to the interior of the container 11 through the opening O. This permits the container 11, after preliminary filling with material that requires further processing, to be evacuated before the cap 12 is sealed to the container 11.

For example, the container 11 may have ingredients that require freeze drying by pulling a vacuum through the opening O. Once there is sufficient vacuum, the cap 12 is depressed into the rim 11r until the base 12b is in contact as shown in the broken away portion of FIG. 1A. In addition, the housing 13 provides an interlock 13k with respect to the base 12b in order to stop the downward positioning of the cap 12 with respect to the container 11.

(B) SECOND EMBODIMENT OF THE INVENTION

As noted above, the housing 13 of cap 12 contains structure for a flow control valve, which is illustrated in the cross-sectional views of FIGS. 2C and 2D. The valve structure within the housing 13 extends from the base 12b along the interior of the inlet stem 13s. As indicated in FIG. 2A, when access to the container 10 is desired, the sub-cap 14s of the tamper evident seal 14 in FIG. 1D is twisted away as shown in FIG. 2A. This permits access to the interior valve 20 of FIG. 2C by the Luer fitting 21 of FIG. 2B. The action of the Luer fitting 21 in operating the valve 20 is illustrated in FIG. 2D. Details of construction and operation for the valve 20 are similar to the embodiment 40 of FIGS. 4A through 4C, which is discussed in detail below.

(B) THIRD EMBODIMENT OF THE INVENTION

In addition to the medicinal bottle 11 of FIG. 1B, the invention can be applied, as shown in FIG. 3, to a standard infusion bag 31. In place of the conventional spikable inlet, a housing 33, similar to the housing 13 of FIG. 1C is attached to the bag 31. Access to the bag 31 is by way of a standard Luer fitting 34 which operates as illustrated for the embodiment of FIGS. 4A through 4C. The Luer fitting 34 is connected to a conduit 35, illustratively plastic tubing, which extends to a check valve 33'. The check valve 33' can be of the kind illustrated in FIGS. 4A through 4C. In the vicinity of the check valve 33' is a needless infusion valve 33", which also can be of the kind illustrated in FIGS. 4A through 4C. While the valves 33" and 33' are joined at a "Y" connection 36, the connection alternatively may be of the manifold type illustrated in co-pending application Ser. No. Ser. No. 07/871,190, filed Apr. 20, 1992. In addition the housing 33 contains a valve structure similar to that of valves 33' and 33".

In the case of the ordinary spiked bag, when the connector is removed after spiking has taken place, there is inevitable leakage because there is nothing to prevent flow from the interior of the bag. In the case of the invention, however, the removal of the Luer fitting 34 does not produce any leakage because the valve of the housing 33 closes the outlet from the bag.

(C) FOURTH EMBODIMENT OF THE INVENTION

The valve 20 of the housing 13 of FIG. 2C, and the valves 33, 33' and 33" of FIG. 3 can take the form of the valve 43 shown in FIG. 4A. The valve 43 is a flow control device with an inlet 44 for the flow of fluid, an outlet 45 connected to the inlet 44 and disposed to serve as a conduit for flow into the inlet 44. A movable and flexible plug 46 seals the inlet 44 and extends to a flexible body 47 for controlling flow by the extent to which the flexible body 47 of the movable plug 46 is buckled as indicated in FIG. 4C. In effect, the combination of the plug 46 and the body 47 form a bell-shaped member with a slotted and fluted side walls. The base of the body 47 terminates in a circumferential base ring 47-r.

In the flow control device 43, the movable plug 46 and the flexible body 47 extend between the inlet 44 and the outlet 45. The flexible body 47 of the moveable plug 46 is expandable laterally with respect to the axis A' of the outlet channel 45 in order to control flow. Consequently the housing 48 has an enlarged expansion chamber 48-1. In addition the housing 48 has a neck 48-2 with exterior Luer threads 48-t and an interior undercut rim 48-r. A ring 46-r of the plug 46 initially seals the plug 46 against the undercut rim 48-r and remains in contact with the interior wall 48-w of the neck 48-2 as the plug is depressed until until the expansion chamber 48-1 is reached. The upper portion of the expansion chamber 48-1 has an undercut 48-u which permits flow into the outlet 45.

For the embodiment of FIG. 4A, the plug 46 has an upper slot 46-s so that when a Luer tip, such as the tip 41 of FIG. 4B is threaded on the neck 48-2, there is no impediment to flow from the interior of the tip 41. This embodiment is particularly useful for relative low pressure infusion of fluids, e.g. by gravity flow from the bag 30 of FIG. 3. It is to be noted that because of the slot 46-*s*, pressure against the outer surface of the plug 46 does not cause a collapse of the plug material which could block the tip 41.

The Luer tip 41 thus permits activation of the control plug by a member external to the flow control device 43 since the plug 46 is seated in the inlet 44 and can be depressed from its seat 48-*s* against the undercut rim 48-*r*.

In effect the control is by a bell-shaped member with its upper portion sealing the inlet, and walls straddling the outlet. The walls are extended legs which are bowed under pressure in the axial direction of the outlet channel. The bell-shaped member has slotted walls which are buckled under pressure. The slotted walls extend from a head sealing the inlet to a base encircling the outlet channel. The head can have a level surface as shown in FIG. 5A at the entrance to the inlet for high pressure anesthetic applications, or an interrupted surface at the entrance to the inlet for infusion.

The flow control device 43 can seal a container of medicinal fluid as shown in FIGS. 1A and 2. Access to the container is achieved by flexing the moveable seal to unseal the container, and the removal of flex restores the seal of the container.

In the method of the invention for controlling fluid flow the steps include (1) sealing the inlet 44 by the flexible stopper 46; and (2) controllably flexing a slotted body 47 extending integrally from the stopper 46 to permit the flow of fluid to the outlet 45.

The method further includes the step of flexing the body 47 of the stopper 46 by applying fluid pressure as indicated in FIG. 5B. Alternatively, the body 47 can be flexed by applying mechanical pressure as shown in FIG. 4B.

The method of the invention also including the step of positioning the stopper at the inlet of the container 10 or 20 for medicinal fluid in order to permit access to the container by flexing the stopper and resealing the container by unflexing the stopper. The step of flexing the stopper includes the lateral expansion of the body 47 with respect to the axis A' of the inlet 44 and the outlet 45.

In a method of fabricating a flow control device by the invention the steps include (a) molding an inlet member 48 having an axis of flow A, a coaxial seat and an expansion chamber; (b) molding an outlet member having the same axis of flow and a coaxial support; (c) inserting an expandable control member into the inlet with respect to the seat; and (e) joining the outlet member to the inlet member with the support for the expandable control member against the outlet member. The method further includes the step of molding the control member of an elastomeric material and, where the control member extends longitudinally, there is the further step of longitudinally slotting the control member. The control member can have a circular body with slots that are uniformly spaced about the body.

The component elements of the various devices can be joined, for example, by ultrasonic welding. The valves of the invention promote sterility by providing ease of accessibility. Prior art valves with recessed stoppers allow antimicrobial agents to accumulate in puddles on the tops of stoppers. Particulate matter may also collect on recessed tops.

(D) FIFTH EMBODIMENT OF THE INVENTION

An alternative flow control device 50 in accordance with the invention is shown in FIG. 5A. The device 50 has the same general structure as the device 40 of FIG. 4A, except that the plug 56 has a level top surface 56s. The device 50 is intended for medical applications which involve the entry of fluids, for example in anesthesia, under relatively high pressures. As a result, after the Luer fitting is attached to the valve as shown in FIG. 5B, the force of the applied fluid causes the plug 56 to move downwardly as show in in FIG. 5C and permit the flow of fluid into the outlet between the ribs 56r in the same fashion as previously illustrated for the embodiment of FIG. 2d.

(E) ADDITIONAL EMBODIMENTS

The embodiments of FIGS. 1A, 2A, 3, 4A and 5A are single port devices. The invention also includes multiple port infusion devices of the kind disclosed in co-pending application Ser. No. 07/871,190, filed Apr. 20, 1992, U.S. Pat. No. 5,289,984 with ports circumferentially mounted with respect to inlet and outlet housings. The individual ports can be similar to those illustrated above and may, or may not, include a flow control diaphragm. In general, however, multiport infusing devices will omit any diaphragm.

It will be understood that the foregoing embodiments are illustrative only and that modifications and adaptations of the invention may be made without departing from its spirit and scope as defined in the appended claims.

What is claimed:

1. A flow control device comprising an inlet at a surface for the flow of fluid;

an outlet connected to said inlet and disposed with respect thereto to serve as a conduit for flow into said inlet; and movable means disposed coextensively with said surface sealing said inlet and having a flexible single-layer and longitudinally-slotted body for controlling flow by the extent to which the flexible body of said movable means is buckled.

2. A flow control device in accordance with claim 1 wherein said movable means extends between said inlet and said outlet; and said single-layer body is expandable laterally and foldable into contact upon itself into opposed bulges with respect to the axis of said outlet in order to control said flow.

3. Apparatus as defined in claim 1 further including means for permitting the activation of the controlling means by a member external to the flow control device by engaging said moveable means which terminates in a plug seated in a base opening of said inlet and which can be depressed from its seat.

4. Apparatus as defined in claim 1 wherein said movable means comprises a bell-shaped member with its upper portion sealing said inlet and having walls perpendicularly connected to a fixed base straddling said outlet.

5. Apparatus as defined in claim 4 wherein said bell-shaped member has slotted and non overlapping walls which are buckled under pressure.

6. A flow control device comprising an inlet for the flow of fluid;

an outlet connected to said inlet and disposed with respect thereto to serve as a conduit for flow into said inlet; and movable means having a head sealing said inlet and a flexible body for controlling flow by the extent to which said flexible body is buckled, comprising a bell-shaped member with a wall containing at least one slot therein extending in the axial direction of said outlet, from said head sealing said inlet to a base encircling said outlet.

7. Apparatus as defined in claim 6 wherein said extending means comprises a member which is bowed under fluid pressure in the axial direction of said outlet.

8. Apparatus as defined in claim 6 wherein said inlet has an entrance and said head has a level surface coextensive with said entrance to said inlet.

9. Apparatus as defined in claim 6 wherein said head has an interrupted surface coextensive with said entrance to said inlet.

10. Apparatus as defined in claim 6 wherein said flow control device seals a closable container of medicinal fluid;

whereby access is achieved by flexing said moveable sealing means to unseal said container and the removal of flex restores the seal of said container.

11. The method of controlling fluid flow which comprises the steps of:

(1) sealing an inlet by a flexible single-layer stopper that is swabbable across said inlet; and (2) controllably flexing said stopper to produce a fold in said layer and permit the flow of said fluid to an outlet.

12. The method of claim 11 further including the step of flexing and circumferentially expanding said stopper into an auxiliary chamber by applying fluid pressure thereto.

13. The method of claim 11 further including the step of flexing said stopper by applying mechanical pressure to the swabbable portion of said stopper.

14. The method of claim 11 further including the step of positioning said stopper at the inlet of a closable container for medicinal fluid in order to permit access to said container by flexing said stopper and resealing of said container by unflexing said stopper.

15. The method of claim 11 wherein the step of flexing said stopper includes the lateral folding thereof into touching contact with itself with respect to axes of said inlet and said outlet.

16. The method of claim 11 further including the step of molding said stopper of an elastomeric material.

17. The method of claim 11 wherein said stopper extends longitudinally, further including the step of longitudinally slotting said stopper.

18. The method of controlling fluid flow which comprises the steps of:

(1) sealing an inlet channel by a swabbable and flexible single-layer stopper; and (2) controllably flexing said stopper to produce a fold in said layer and permit the flow of said fluid to an outlet;

wherein said stopper has a body that extends longitudinally, further including the step of longitudinally slotting said stopper with slots that are elongated and uniformly spaced about said body.

* * * * *